US012728066B2

(12) United States Patent
Wersland et al.

(10) Patent No.: US 12,728,066 B2
(45) Date of Patent: Sep. 8, 2026

(54) PNEUMATIC COMPRESSION DEVICE WITH VIBRATION AND TEMPERATURE CONTROL

(71) Applicant: THERABODY, INC., Los Angeles, CA (US)

(72) Inventors: Jason Wersland, Los Angeles, CA (US); Benjamin Nazarian, Beverly Hills, CA (US); Jaime Sanchez Solana, Los Angeles, CA (US); Eduardo Merino, Los Angeles, CA (US); Washington Alexander Silva Garces, Los Angeles, CA (US); Brian Carberry, Los Angeles, CA (US); Tudor Besleaga, East Sussex (GB)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/059,247

(22) Filed: Nov. 28, 2022

(65) Prior Publication Data

US 2023/0165746 A1 Jun. 1, 2023

Related U.S. Application Data

(63) Continuation of application No. 17/554,416, filed on Dec. 17, 2021, now Pat. No. 11,510,844.

(Continued)

(51) Int. Cl.

*A61H 9/00* (2006.01)
*A61F 5/01* (2006.01)

(Continued)

(52) U.S. Cl.

CPC ............ *A61H 9/0092* (2013.01); *A61F 5/01* (2013.01); *A61F 5/012* (2013.01);

(Continued)

(58) Field of Classification Search

CPC . A61H 9/0092; A61H 2201/0207; A61F 5/01; A61F 5/012; A61F 5/05816;

(Continued)

(56) References Cited

U.S. PATENT DOCUMENTS

| | | | |
|---|---|---|---|
| 1,545,027 | A | 7/1925 | Ashlock |
| D143,678 | S | 1/1946 | Snyder et al. |

(Continued)

FOREIGN PATENT DOCUMENTS

| | | | |
|---|---|---|---|
| CA | 178767 | S | 9/2018 |
| CN | 201239336 | Y | 5/2009 |

(Continued)

OTHER PUBLICATIONS alexnld.com: "Adjustable Waist Support Belt 3 Modes Heating Back Massage Band Lumbar Brace," Available at least as early as Dec. 6, 2021, 18 Pages, Retrieved from URL: https://alexnld.com/product/adjustable-waist-support-belt-3-modes-heating-back-massage-band-lumbar-brace/.

(Continued)

*Primary Examiner* — Carl H Layno
*Assistant Examiner* — Aya Ziad Bakkar
(74) *Attorney, Agent, or Firm* — Sterne, Kessler, Goldstein & Fox P.L.L.C.

(57) ABSTRACT

A pneumatic compression assembly that includes a sleeve having an outer layer and an inner layer that defines a sleeve interior configured to receive a body part of a user, and at least a first vibration assembly configured to provide vibration to the body part of the user. A plurality of inflatable compartments are arranged longitudinally along the sleeve between the inner layer and the outer layer. The first vibration assembly includes a plurality of vibration motors positioned between the inner layer and the outer layer of the sleeve.

19 Claims, 10 Drawing Sheets

Related U.S. Application Data

(60) Provisional application No. 63/238,354, filed on Aug. 30, 2021, provisional application No. 63/167,533, filed on Mar. 29, 2021, provisional application No. 63/126,954, filed on Dec. 17, 2020, provisional application No. 63/126,968, filed on Dec. 17, 2020.

(51) Int. Cl.
*A61F 5/058* (2006.01)
*A61H 23/02* (2006.01)
*A61N 5/00* (2006.01)
*A61N 5/06* (2006.01)

(52) U.S. Cl.
CPC ......... *A61F 5/05816* (2013.01); *A61H 23/02* (2013.01); *A61N 5/0625* (2013.01); *A61H 2201/0207* (2013.01); *A61N 2005/005* (2013.01); *A61N 2005/0626* (2013.01); *A61N 2005/066* (2013.01); *A61N 2005/0666* (2013.01)

(58) Field of Classification Search
CPC ............ A61N 5/0625; A61N 2005/005; A61N 2005/0626; A61N 2005/066; A61N 2005/0666
See application file for complete search history.

(56) References Cited

U.S. PATENT DOCUMENTS

| | | | |
|---|---|---|---|
| 2,987,334 | A | 6/1961 | Wendling |
| 3,705,579 | A | 12/1972 | Morini et al. |
| D230,522 | S | 2/1974 | Rothman |
| 4,046,142 | A | 9/1977 | Whitney |
| D265,002 | S | 6/1982 | Hubner |
| 4,976,706 | A | 12/1990 | Aki et al. |
| 5,014,681 | A | 5/1991 | Heeman et al. |
| 5,092,317 | A | 3/1992 | Zelikovski |
| 5,103,809 | A | 4/1992 | DeLuca et al. |
| D353,205 | S | 12/1994 | Canavan |
| D417,284 | S | 11/1999 | Kondo |
| 6,093,164 | A | 7/2000 | Davis et al. |
| D439,984 | S | 4/2001 | Thach |
| 6,406,445 | B1 | 6/2002 | Ben-Nun |
| 6,558,338 | B1 | 5/2003 | Wasserman |
| 6,591,142 | B1 | 7/2003 | Dea |
| D479,877 | S | 9/2003 | Lee et al. |
| 6,823,762 | B2 | 11/2004 | Hu |
| 6,846,295 | B1 | 1/2005 | Ben-Nun |
| D518,895 | S | 4/2006 | Weaver, II et al. |
| 7,022,093 | B2 | 4/2006 | Smith et al. |
| 7,044,924 | B1 | 5/2006 | Roth et al. |
| 7,207,953 | B1 | 4/2007 | Goicaj |
| D554,268 | S | 10/2007 | Harding |
| D554,761 | S | 11/2007 | Marin |
| D571,923 | S | 6/2008 | Roberts |
| 7,431,706 | B2 | 10/2008 | Louis |
| D582,047 | S | 12/2008 | Yim |
| 7,509,692 | B2 | 3/2009 | Elkins et al. |
| D598,556 | S | 8/2009 | Chen |
| D608,006 | S | 1/2010 | Avitable et al. |
| D613,870 | S | 4/2010 | Shust |
| D635,682 | S | 4/2011 | Chiang |
| 7,927,259 | B1 | 4/2011 | Rix |
| 7,927,294 | B2 | 4/2011 | Kamimura et al. |
| D638,948 | S | 5/2011 | Janzon |
| D659,644 | S | 5/2012 | Gretz |
| 8,313,450 | B2 | 11/2012 | Ben-Nun |
| D678,531 | S | 3/2013 | Patil |
| D695,902 | S | 12/2013 | Daniels et al. |
| 8,622,943 | B2 | 1/2014 | Ben-Nun |
| D704,848 | S | 5/2014 | Thomas et al. |
| 8,764,688 | B1 | 7/2014 | Nauman et al. |
| 8,777,881 | B2 | 7/2014 | Tsai |
| D712,052 | S | 8/2014 | Thomas et al. |
| D716,457 | S | 10/2014 | Brefka et al. |
| 9,017,273 | B2 | 4/2015 | Burbank et al. |
| D735,873 | S | 8/2015 | Brefka et al. |
| 9,125,442 | B2 | 9/2015 | Brown |
| D751,720 | S | 3/2016 | Williams |
| D754,355 | S | 4/2016 | Ganapathy et al. |
| D756,180 | S | 5/2016 | Chen |
| D762,869 | S | 8/2016 | Beckman et al. |
| D764,672 | S | 8/2016 | Vosch et al. |
| 9,414,954 | B2 | 8/2016 | Brown |
| 9,549,870 | B2 | 1/2017 | Shafieloo |
| D786,447 | S | 5/2017 | Bigelow et al. |
| D800,326 | S | 10/2017 | Cox |
| 9,849,024 | B2 | 12/2017 | Mandel |
| D806,888 | S | 1/2018 | Cheng et al. |
| D810,311 | S | 2/2018 | Chen |
| D811,613 | S | 2/2018 | Marton et al. |
| D811,614 | S | 2/2018 | Marton et al. |
| 9,889,066 | B2 | 2/2018 | Danby et al. |
| 9,901,510 | B2 | 2/2018 | Smith |
| D817,732 | S | 5/2018 | Rettler |
| D820,994 | S | 6/2018 | Trapp |
| D822,221 | S | 7/2018 | Huth et al. |
| D831,221 | S | 10/2018 | Smith |
| 10,123,937 | B2 | 11/2018 | Pisharodi et al. |
| 10,159,623 | B2 | 12/2018 | Leftly |
| D837,394 | S | 1/2019 | Cryan et al. |
| D837,395 | S | 1/2019 | Gan |
| D841,178 | S | 2/2019 | Lazarides et al. |
| D841,825 | S | 2/2019 | Rogers |
| 10,245,208 | B2 | 4/2019 | Macguinness |
| 10,314,762 | B1 | 6/2019 | Marton et al. |
| 10,406,024 | B2 | 9/2019 | Evans et al. |
| D863,573 | S | 10/2019 | Ito et al. |
| D865,986 | S | 11/2019 | Cryan et al. |
| 10,493,264 | B1 | 12/2019 | Lefkovitz |
| 10,555,681 | B2 | 2/2020 | Sun |
| 10,632,040 | B2 | 4/2020 | Muench et al. |
| D886,302 | S | 6/2020 | Raghavan et al. |
| D890,933 | S | 7/2020 | Shurtliff et al. |
| D891,626 | S | 7/2020 | Xu |
| 10,779,764 | B2 | 9/2020 | Marlinski |
| D905,253 | S | 12/2020 | Hubelbank |
| D910,858 | S | 2/2021 | Marton et al. |
| D917,054 | S | 4/2021 | Woo |
| D923,184 | S | 6/2021 | Li |
| D928,974 | S | 8/2021 | Zulkosky et al. |
| D932,035 | S | 9/2021 | McDonough et al. |
| D932,042 | S | 9/2021 | Hu |
| D932,638 | S | 10/2021 | McDonough et al. |
| D932,639 | S | 10/2021 | McDonough et al. |
| D932,640 | S | 10/2021 | McDonough et al. |
| D937,426 | S | 11/2021 | Cordle |
| D950,740 | S | 5/2022 | Caneppele et al. |
| D953,550 | S | 5/2022 | Li |
| D957,651 | S | 7/2022 | Williams et al. |
| D957,654 | S | 7/2022 | Savchuk |
| D961,889 | S | 8/2022 | Chen |
| 11,510,844 | B2 | 11/2022 | Wersland et al. |
| 11,564,831 | B1 | 1/2023 | Aguiar et al. |
| 2004/0091663 | A1 | 5/2004 | Jang |
| 2005/0075593 | A1 | 4/2005 | Smith et al. |
| 2005/0193742 | A1 | 9/2005 | Arnold |
| 2005/0261641 | A1 | 11/2005 | Warchol et al. |
| 2007/0255187 | A1 | 11/2007 | Branch |
| 2008/0188915 | A1 | 8/2008 | Mills et al. |
| 2010/0249637 | A1 | 9/2010 | Walter et al. |
| 2011/0000516 | A1 | 1/2011 | Hershberger et al. |
| 2011/0233185 | A1 | 9/2011 | Augustine et al. |
| 2012/0023785 | A1 | 2/2012 | Barnes et al. |
| 2013/0030331 | A1 | 1/2013 | Quisenberry et al. |
| 2013/0085552 | A1 | 4/2013 | Mandel |
| 2014/0276257 | A1 | 9/2014 | Santa Maria et al. |
| 2014/0316311 | A1 | 10/2014 | Nauman et al. |
| 2014/0350441 | A1 | 11/2014 | Shafieloo |
| 2014/0364778 | A1 | 12/2014 | Leftly et al. |
| 2015/0174002 | A1 | 6/2015 | Burbank et al. |
| 2015/0223975 | A1 | 8/2015 | Anderson et al. |

(56) References Cited

U.S. PATENT DOCUMENTS

| | | | | |
|---|---|---|---|---|
| 2016/0058657 | A1 | 3/2016 | Lal et al. | |
| 2016/0089299 | A1 | 3/2016 | Munoz | |
| 2016/0135517 | A1 | 5/2016 | Silverberg | |
| 2016/0228325 | A1 | 8/2016 | Kologrivov et al. | |
| 2016/0331631 | A1 | 11/2016 | Odi | |
| 2016/0346153 | A1 | 12/2016 | Hodges, IV | |
| 2016/0367425 | A1 | 12/2016 | Wersland | |
| 2017/0014255 | A1 | 1/2017 | Booker | |
| 2017/0042754 | A1 | 2/2017 | Fowers et al. | |
| 2017/0113039 | A1 | 4/2017 | Tuan | |
| 2017/0119620 | A1 | 5/2017 | Trapp | |
| 2017/0273830 | A1 | 9/2017 | Hitschmann | |
| 2017/0280682 | A1 | 10/2017 | Ruetenik | |
| 2017/0290736 | A1 | 10/2017 | Idris | |
| 2017/0304145 | A1 | 10/2017 | Pepe | |
| 2018/0042761 | A1 | 2/2018 | Smith et al. | |
| 2018/0042810 | A1 | 2/2018 | Nguyen | |
| 2018/0065517 | A1* | 3/2018 | Kuhley | A61H 23/02 |
| 2018/0140506 | A1 | 5/2018 | Smith et al. | |
| 2018/0141188 | A1 | 5/2018 | Lai | |
| 2018/0147086 | A1 | 5/2018 | Evans et al. | |
| 2018/0228689 | A1* | 8/2018 | Lach | A61H 39/007 |
| 2018/0303704 | A1 | 10/2018 | Idris | |
| 2018/0325724 | A1 | 11/2018 | Kilbey | |
| 2019/0015289 | A1 | 1/2019 | Grimoldby et al. | |
| 2019/0070068 | A1 | 3/2019 | Pisharodi et al. | |
| 2019/0151190 | A1 | 5/2019 | Burbank et al. | |
| 2019/0183724 | A1 | 6/2019 | Sifferlin | |
| 2019/0350752 | A1 | 11/2019 | Aguiar et al. | |
| 2020/0061316 | A1 | 2/2020 | Inoue et al. | |
| 2020/0068964 | A1 | 3/2020 | Brandt et al. | |
| 2020/0078261 | A1 | 3/2020 | Duvall | |
| 2020/0113773 | A1 | 4/2020 | Ramanan et al. | |
| 2020/0214927 | A1 | 7/2020 | Clowney et al. | |
| 2020/0230021 | A1 | 7/2020 | Pisharodi et al. | |
| 2020/0237607 | A1* | 7/2020 | Ramanan | A61H 9/0092 |
| 2020/0253813 | A1 | 8/2020 | Kuhns | |
| 2020/0268592 | A1 | 8/2020 | Johnson et al. | |
| 2020/0368061 | A1 | 11/2020 | Levinson et al. | |
| 2021/0052430 | A1 | 2/2021 | Riley | |
| 2021/0330539 | A1 | 10/2021 | Faussett | |
| 2022/0192868 | A1 | 6/2022 | Wersland et al. | |

FOREIGN PATENT DOCUMENTS

| | | | | | |
|---|---|---|---|---|---|
| CN | 301664182 | S | | 9/2011 | |
| CN | 301695895 | | | 10/2011 | |
| CN | 301771075 | | | 12/2011 | |
| CN | 202637439 | U | | 1/2013 | |
| CN | 103284874 | A | * | 9/2013 | |
| CN | 204048138 | U | | 12/2014 | |
| CN | 303250924 | S | | 6/2015 | |
| CN | 303250929 | S | | 6/2015 | |
| CN | 303679907 | | | 5/2016 | |
| CN | 205285020 | U | | 6/2016 | |
| CN | 304091502 | | | 3/2017 | |
| CN | 106691810 | A | | 5/2017 | |
| CN | 304124110 | | | 5/2017 | |
| CN | 106859949 | A | | 6/2017 | |
| CN | 304223351 | | | 7/2017 | |
| CN | 304334066 | | | 10/2017 | |
| CN | 304364250 | | | 11/2017 | |
| CN | 304561844 | S | | 3/2018 | |
| CN | 207855923 | U | | 9/2018 | |
| CN | 109528473 | A | | 3/2019 | |
| CN | 305105930 | | | 4/2019 | |
| CN | 305121011 | | | 4/2019 | |
| CN | 209059904 | U | | 7/2019 | |
| CN | 110131812 | A | | 8/2019 | |
| CN | 305493698 | | | 12/2019 | |
| CN | 305493699 | | | 12/2019 | |
| CN | 305511388 | | | 12/2019 | |
| CN | 305531856 | | | 1/2020 | |
| CN | 305539686 | | | 1/2020 | |
| CN | 305635976 | | | 3/2020 | |
| CN | 305795905 | | | 5/2020 | |
| CN | 305796012 | | | 5/2020 | |
| CN | 305796013 | | | 5/2020 | |
| CN | 306006372 | | | 8/2020 | |
| CN | 306067989 | | | 9/2020 | |
| CN | 306068005 | | | 9/2020 | |
| CN | 306073089 | | | 9/2020 | |
| CN | 108514470 | B | * | 10/2020 | A61F 5/40 |
| CN | 212038208 | U | | 12/2020 | |
| CN | 306606113 | | | 6/2021 | |
| CN | 306651421 | | | 6/2021 | |
| CN | 306981442 | | | 12/2021 | |
| CN | 306981451 | | | 12/2021 | |
| CN | 307029685 | | | 12/2021 | |
| CN | 307633505 | | | 11/2022 | |
| CN | 307653347 | | | 11/2022 | |
| EM | EU008789861-0001 | | | 12/2021 | |
| EM | EU009010564-0001 | | | 5/2022 | |
| EM | EU009010564-0002 | | | 5/2022 | |
| EM | EU009010564-0006 | | | 5/2022 | |
| EM | EU009010564-0007 | | | 5/2022 | |
| EP | 1009355 | B1 | | 11/2003 | |
| HK | 2117964 | | | 12/2021 | |
| JP | S5428491 | A | | 3/1979 | |
| JP | H0447440 | U | | 4/1992 | |
| JP | 2000189525 | A | | 7/2000 | |
| JP | D1086129 | | | 9/2000 | |
| JP | D1355211 | | | 4/2009 | |
| JP | D1355212 | | | 4/2009 | |
| JP | D1395716 | | | 8/2010 | |
| JP | 2011502369 | A | | 1/2011 | |
| JP | D1444377 | | | 6/2012 | |
| JP | D1456095 | | | 11/2012 | |
| JP | 5129032 | B2 | | 1/2013 | |
| JP | D1483906 | | | 11/2013 | |
| JP | 2014511240 | A | | 5/2014 | |
| JP | D1562309 | | | 11/2016 | |
| JP | D1625637 | | | 3/2019 | |
| JP | D1635963 | | | 7/2019 | |
| KR | 200197414 | Y1 | | 11/2000 | |
| KR | 300388708.0001 | | | 8/2006 | |
| KR | 20090005341 | U | | 6/2009 | |
| KR | 100992766 | B1 | | 11/2010 | |
| KR | 101162978 | B1 | | 7/2012 | |
| KR | 300659290 | | | 9/2012 | |
| KR | 20120100036 | A | | 9/2012 | |
| KR | 300685526 | | | 3/2013 | |
| KR | 300688355 | | | 4/2013 | |
| KR | 300777431 | | | 12/2014 | |
| KR | 300786426 | | | 3/2015 | |
| KR | 20170108550 | A | | 9/2017 | |
| KR | 300941258 | | | 1/2018 | |
| KR | 300959951 | | | 6/2018 | |
| KR | 301075396 | | | 9/2020 | |
| KR | 301082314 | | | 11/2020 | |
| KR | 301109767 | | | 5/2021 | |
| KR | 301165063 | | | 5/2022 | |
| RU | 00129403 | | | 1/2022 | |
| TW | I359657 | B | | 3/2012 | |
| WO | WO-2016198904 | A1 | | 12/2016 | |
| WO | WO-2018064220 | A1 | | 4/2018 | |
| WO | WO-2018230930 | A1 | * | 12/2018 | A61H 23/02 |
| WO | 2019018246 | A2 | | 1/2019 | |
| WO | WO-2022133209 | A1 | | 6/2022 | |
| WO | WO-2023034824 | A1 | | 3/2023 | |

OTHER PUBLICATIONS

Amazon: "RecoveryTherm Back—Hot Vibration Back and Core Wrap for Athletes—Advanced Hot Vibration for Back Pain Relief Wrap with Cryothermal Technology—One Size Fits All", Date First Available on Sep. 20, 2022, 02 Pages, Retrieved from URL: https://www.amazon.com/RecoveryTherm-Back-Vibration-Cryothermal-Technology/dp/BOB8GRL7LR/ref=cm_cr_arp_d_product_top?ie=UTF8.

Amazon: "RecoveryTherm Knee—Contrast Therapy Wrap—Hot & Cold Vibration Recovery Knee Wrap for Athletes—Advanced Con-

(56) References Cited

OTHER PUBLICATIONS trast Therapy for Knee Pain Relief Wrap with Cryothermal Technology—One Size Fits All," Date First Available on Aug. 3, 2022, 03 Pages, Retrieved from URL: https://www.amazon.com/RecoveryTherm-Knee-Vibration-Cryothermal-Technology/dp/BOB8GCB/YF/ref=cm_cr_arp_d_product_topie=UTF8.
Anthony Katz, "The Raptor: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.
Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.
Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).
fsastore.com: "Battle Creek Embrace Relief Knee Wrap," Available at least as early as 2020, 2021, 19 Pages, Retrieved from URL: https://fsastore.com/battle-creek-embrace-relief-knee-wrap/29568.html.
Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.
Hotsnapz: "Back Belt Set with Free Extra Reusable Heat Pad," hotsnapz.com, Available at least as early as 2022, 11 Pages, Retrieved from URL: https://hotsnapz.com/products/hotsnapz-back-belt-set-with-free-extra-heat-pack.
hyperice.com: "Hyperice X," Available at least as early as Sep. 8, 2021, 10 Pages, Retrieved from URL: https://hyperice.com/products/hyperice-x//?wickedsource=google&wickedid=EAlaIQ.obChMlo_D5z_-4-wIV9Y5bCh284gf8EAQ.YByABEgLiRvD_BwE&wickedid=&wcid=17299137048&wv=4&gclid=EAlalQobChMlo_D5z_-4-wIV9Y5bCh284gf8EAQ.YByABEgLiRvD_BwE.
International Search Report and Written Opinion for International Application No. PCT/US2021/064027, mailed Mar. 10, 2022, 19 Pages.
International Search Report and Written Opinion for International Application No. PCT/US2021/064048, mailed Mar. 9, 2022, 9 Pages.
International Search Report and Written Opinion for International Application No. PCT/US2022/075699, mailed Jan. 11, 2023, 8 Pages.
KT Tape: "KT Recovery+ Ice/Heat Wrap," kttape.com, Available at least as early as Jun. 21, 2021, 06 Pages, Retrieved from URL: https://www.kttape.com/products/kt-recovery-ice-heat-wrap.
Therabody: "RecoveryTherm Hot and Cold Vibration Knee," Accessed on Jan. 30, 2023, 03 Pages, Retrieved from URL: https://www.therabody.com/us/en-us/recoverytherm-knee-massager-compression.htmlcgid=therabody-recovery-devices#start=1.
Therabody: "RecoveryTherm Hot Vibration Back and Core Wrap for Athletes—Advanced Hot Vibration for Back Pain Relief Wrap with Cryothermal Technology—One Size Fits All," Accessed on Jan. 30, 2023, 02 Pages, Retrieved from URL: https://www.therabody.com/us/en-us/recoverytherm-core-lower-back-massager-compression.html?cgid=therabody-recovery-devices#start=1.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.
Youtube: "Therabody RecoveryTherm Knee Sleeve Review—Hot, Cold, Vibration," Published on Dec. 22, 2022, 01 Page, Retrieved from URL: https://www.youtube.com/watch?v=-dHbFc_LJfw.
International Search Report and Written Opinion of the International Searching Authority directed to International Patent Application No. PCT/US2023/085190, mailed Jun. 12, 2024, 17 pages.
International Search Report and Written Opinion of the International Searching Authority, directed to related International Application No. GB2418585.2, mailed Mar. 10, 2025, 4 pages.
Supplementary Partial European Search Report directed to European Application No. EP22865745.8, dated Jun. 18, 2025, 16 pages.
International Search Report and Written Opinion directed to Great Britain Application No. GB2511118.8, dated Jul. 31, 2025, 7 pages.
Office Action issued in Chinese Application No. 202180085190.X, mailed Jan. 21, 2026, 22 pages.

* cited by examiner

PNEUMATIC COMPRESSION DEVICE WITH VIBRATION AND TEMPERATURE CONTROL

CROSS-REFERENCE TO RELATED APPLICATIONS

This application is a continuation of U.S. application Ser. No. 17/554,416, now U.S. Pat. No. 11,510,844, filed Dec. 17, 2021, which claims the benefit of U.S. Provisional Application No. 63/238,354, filed Aug. 30, 2021, U.S. Provisional Application No. 63/167,533, filed Mar. 29, 2021, U.S. Provisional Patent Application No. 63/126,954, filed Dec. 17, 2020, and U.S. Provisional Application No. 63/126,968, filed Dec. 17, 2020, the entireties of which are incorporated by reference herein.

FIELD OF THE INVENTION

The present invention relates to a pneumatic compression assembly, and more particularly to a pneumatic compression assembly with one or more therapeutic features, such as temperature control, vibration, pneumatic compression, infrared and the like.

BACKGROUND OF THE INVENTION

Pneumatic compression devices are characterized by bulky, invasive devices and typically only include compression without focusing on any other therapeutic technology, such as temperature, vibration or the like.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a pneumatic compression assembly that includes a sleeve that includes an outer layer and an inner layer that defines a sleeve interior configured to receive a body part of a user, a plurality of inflatable compartments arranged longitudinally along the sleeve between the inner layer and the outer layer, and at least a first vibration assembly configured to provide vibration to the body part of the user. The first vibration assembly includes a plurality of vibration motors positioned between the inner layer and the outer layer of the sleeve. In a preferred embodiment, the first vibration assembly includes a first carrier layer and a first motor securement member. The first motor securement member secures at least a first of the plurality of vibration motors to the first carrier layer. Preferably, the first carrier layer includes a first carrier layer motor opening defined therein. The first motor securement member includes upper and lower securing portions and a motor portion extending between the upper and lower securing portions. The upper and lower securing portions are positioned on a first side of the first carrier layer and wherein at least a portion of the motor portion of the first securement member and at least a portion of the vibration motor extend through the first carrier layer motor opening.

In a preferred embodiment, the first carrier layer includes one or more heating elements thereon. Preferably, a second carrier layer is positioned between the inner layer and the outer layer of the sleeve. The second carrier layer is secured to the first carrier layer to form a carrier assembly and sandwich the heating element therebetween. The second carrier layer includes a second carrier layer motor opening defined therein, the upper and lower securing portions are positioned on a first side of the carrier assembly, and at least a portion of the vibration portion of the first securement member and at least a portion of the vibration motor extend through the first and second vibration openings. Preferably, at least one of the first and second carrier layers is a far infrared layer. Preferably, a reflective foil layer is positioned between the far infrared layer and the outer layer of the sleeve.

In a preferred embodiment, the pneumatic compression assembly includes at least a first heating assembly configured to provide heat to the body part of the user. The first heating assembly is positioned between the inner layer and the outer layer of the sleeve. The first heating assembly can be any of the components or layers discussed herein (e.g., the first and/or second carrier layers) that include heating elements thereon or therein.

In accordance with another aspect of the present invention there is provided a pneumatic compression assembly that includes a sleeve that includes an outer layer and an inner layer that defines a sleeve interior configured to receive a body part of a user, a plurality of inflatable compartments arranged longitudinally along the sleeve between the inner layer and the outer layer, and a temperature control module coupled to or within the sleeve. The temperature control module includes a housing, a controllable temperature element, and a spreader member. A lower surface of the spreader member is positioned to contact the user's body part, and the controllable temperature element is configured to transfer thermal energy to an upper surface of the spreader member. In a preferred embodiment, the temperature control module includes a heat sink that is positioned within a first of the plurality of inflatable compartments so that air moving through the first inflatable compartment pulls or dissipates heat from the heat sink. Preferably, the temperature control module includes at least a first finger spreader pivotably attached to the spreader member. The spreader member is configured to conduct thermal energy to the first finger spreader.

The present invention is a pneumatic compression device that can be used for recovery after physical activities, among other uses. Pneumatic compression devices are known. For example, see U.S. Pat. Nos. 5,014,681, 5,092,317, 6,406,445, 6,558,338, 6,846,295, 8,313,450, and 8,622,943, each of which are incorporated herein by reference in its entirety.

Pneumatic compression applied to the human body often includes a fluid pump module (main unit) that is connected to an inflatable garment (i.e., full leg boots, core, or arm and shoulder sleeve) through one or multiple pipes. The air pumped from the module flows into the garment inflating it and compressing the body part that is inside. There are many different methods for inflating the garment and determining how much pressure is applied and how quickly it inflates and deflates. Many boots are divided into four compartments that inflate sequentially starting with the lowest one (foot) and going up towards the hips.

In the present invention, one or more of vibration, heating, cooling and other features are included in a pneumatic compression device to provide more options for recovery. In a preferred embodiment, the pneumatic compression device or assembly includes heating and cooling modules within the device and the devices can be cooled via the air flow generated by the inflation pump to dissipate heat from the module and specifically the peltier module and/or heat sink.

In a preferred embodiment, the pneumatic compression assembly includes a sleeve that includes a plurality of cells, chambers or compartments defined therein. In a preferred embodiment, the compartments inflatable sequentially to provide compression to a user's foot and leg (when the invention is embodied in a boot). It will be appreciated that the pneumatic compression assembly can be sized, designed and utilized on any body part.

In a preferred embodiment, one or more temperature control modules are included or positioned in one or more of the compartments. The temperature control modules may include a module housing that houses a fan, heat sink and peltier module. In a preferred embodiment, there is no garment or fabric layer between the temperature control module and the user's skin. Instead, the bottom layer or lower surface of the temperature control module or some other heat conductive portion or material contacts the user's skin. In another embodiment, a layer can be included between the module and the user's skin. In a preferred embodiment, the temperature control module may also include one or more vibration motors or devices (that may include a counterweight or eccentric weight) therein.

In another preferred embodiment, the fan and all or part of the module housing of the temperature control module can be omitted and the air moving within the compartment as a result of the air pump. In another embodiment the heat sink can also be omitted with the air in the sleeve cooling the peltier device. As shown, the sleeve includes an inner layer and an outer layer.

In another preferred embodiment of a temperature control module that includes a concave module structure or bottom surface so that it can adapt to the contour of different portions of the body, such as the thigh, calf, etc. Preferably, the module housing includes a lower portion that includes the concave surface on a bottom thereof. The lower portion also includes a conductive member that conducts heat or cold from the peltier device to the concave bottom surface. The upper and lower housing portions of the peltier housing define a motor recess.

In another embodiment, the temperature control module may include the fan next to the heat sink instead of on top of the heat sink. All temperature control modules herein include vents or openings in the module housing to allow heat to be dissipated therefrom. It will be appreciated that the module housing or a portion thereof can be omitted or the fans can be omitted (or can remain included) so that the air movement within the sleeve can cool the components of the module, as needed.

In another embodiment, hot and/or cold air can be pumped directly into the sleeve or into individual compartments to provide hot and cold therapy. In another embodiment, one or more pumps or compressors can be incorporated into the sleeve (to inflate the sleeve or individual compartments) as opposed to being separate therefrom.

In a preferred embodiment the pneumatic compression assembly includes infrared LEDs or an infrared fabric that are embedded in positioned on or otherwise associated with the outer or upper layer and that shine or emit light through the compartment(s) and through the inner layer that is clear or at least partially clear so that the infrared light reaches the wearer's skin. The infrared lights can be positioned anywhere or in the sleeve or compartment (e.g., on the inner layer, the module or somewhere else in the compartment). Vibration devices/motors 18 may also be embedded on or in the inner layer for providing vibration to the user. Vibration devices can be positioned as desired throughout the sleeve. The vibration devices can be arranged in patterns to help with or stimulate blood flow and to aid with recovery.

In a preferred embodiment of the present invention, the system includes the ability to insert liquid nitrogen or another cooling fluid therein to cool the air that gets pumped into the compression sleeve. This can create a homogeneous and fast cooling feeling when using the pneumatic compression device. In a preferred embodiment, the cooling fluid is added to or included in the compressor module. Preferably, the compressor module or pump has a cavity therein designed to receive and the replaceable liquid bottle where it can be connected for use.

In use, when the user selects the cooling mode the valve of the bottle is opened and the liquid nitrogen flows from tubes that go from the compressor to the compartments of the sleeve. The low temperature provides a cool feeling throughout the entire surface of the boot/garment.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
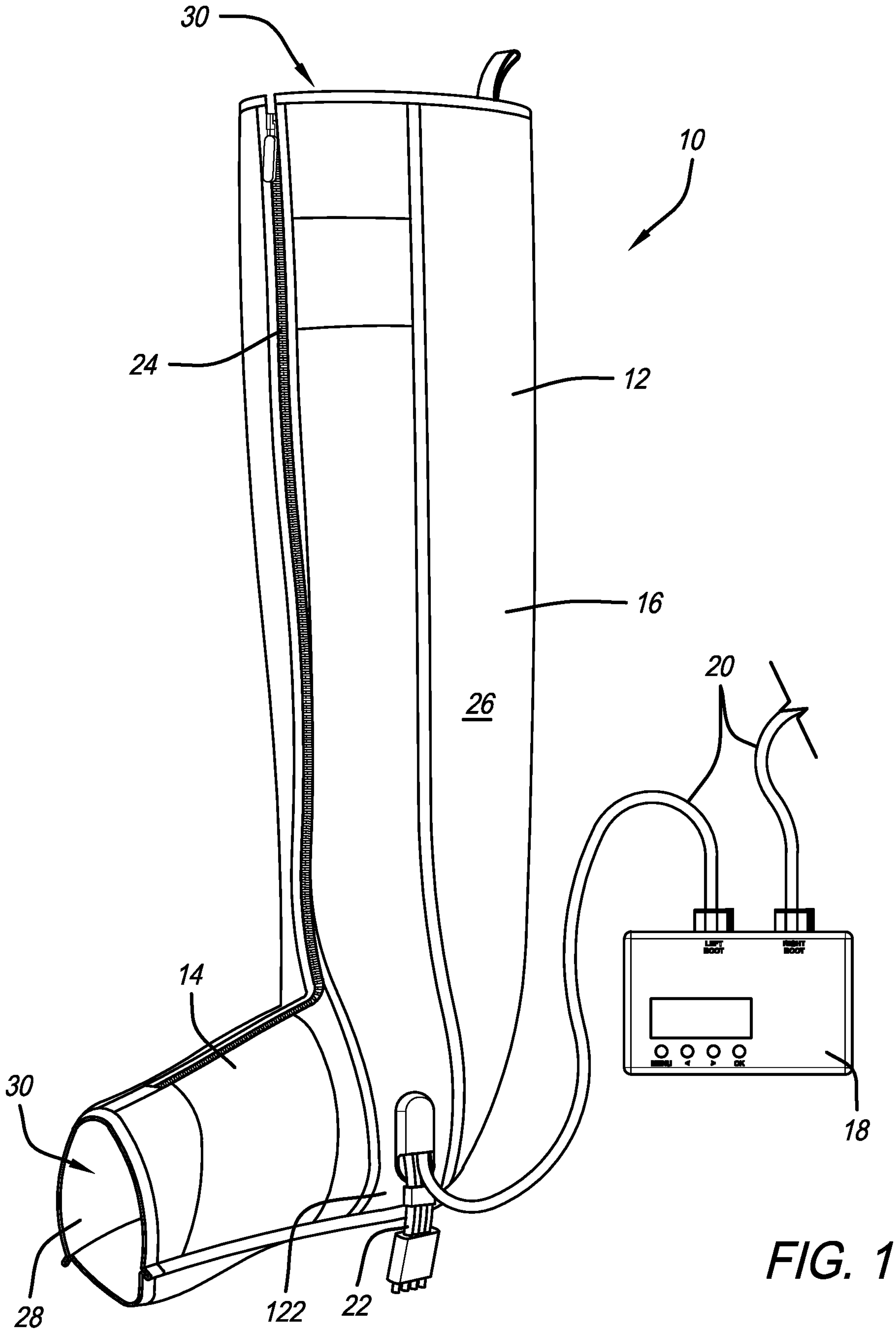
FIG. 1 is a perspective view of a pneumatic compression assembly in accordance with a preferred embodiment of the present invention attached thereto.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Described herein and shown in FIGS. 1-7 is a pneumatic compression garment or assembly 10 that preferably includes one or more of vibration, heating/cooling and infrared in addition to pneumatic compression therapy. FIGS. 1-7 show the pneumatic compression assembly embodied in a closeable sleeve or boot that is configured to be used or worn on a user's leg. However, it will be appreciated that this is not a limitation on the present invention and the pneumatic compression assembly 10 can be any type of wearable garment, wrap or sleeve that is worn around or against a user's body part or body parts.

FIG. 1 shows the pneumatic compression assembly 10 including a sleeve 12, a foot portion 14, a leg portion 16 and a system controller 18 with electrical cabling 20 for electrical and data communication with the various portions, components or assemblies discussed herein. Hoses 22 for connection to a pneumatic pump and inflation of the inflatable compartments are also shown. The sleeve 12 also includes a closure system, such as a zipper 24.

As shown in FIGS. 2-5, in a preferred embodiment, the sleeve 23 includes an outer layer 26 and an inner 28 layer that defines a sleeve interior 30 configured to receive a body part of a user. A plurality of inflatable compartments 32 are arranged longitudinally along the sleeve 23 between the inner layer 28 and the outer layer 26. The plurality of inflatable compartments 32, together with any layers related thereto may be referred to herein as the pneumatic compression portion 34.

In a preferred embodiment, the pneumatic compression assembly 10 includes first, second and third vibration assemblies 36, 38 and 40. The first vibration assembly 36 is associated with the foot portion 14, the second vibration assembly 38 is associated with the lower leg and the third vibration assembly 40 is associated with the upper leg. Each of the vibration assemblies include one or more vibration motors 42 or vibration devices associated therewith.

Each of the first, second and third vibration assemblies 36, 38 and 40 includes first and second carrier layers 44 and 46 that are preferably made of fabric. In a preferred, one of the first and second carrier layers 44 and 46 is a far infrared or FIR layer. In other words, the layer includes a far infrared fabric (or can include far infrared/infrared LEDs). In another embodiment, the carrier layer may not include FIR. In a preferred embodiment, the other of the first and second carrier layers 44 and 46 includes one or more heating elements 48 thereon. The heating elements 48 are positioned or sandwiched between the first and second carrier layers 44 and 46, and the first and second carrier layers 44 and 46 are secured to one another to form a carrier assembly 49. In a preferred embodiment, the heating elements 48 are embroidered on the first or second carrier layer. However, the heating elements can be attached using other methods, such as adhering, gluing, etc. In a preferred embodiment, the motor securement members and/or inner layer are heat pressed to the carrier assembly and all of the various layers are sewn to one another to create the sleeve. In a preferred embodiment, each of the first carrier layers 44 or heating panel (e.g., foot, calf and thigh) have the heating elements 48 embroidered thereon. The second carrier layer 46, which may be a Kymira FIR fabric is sewn onto the first carrier layer 44, covering the heating elements 48. Thermistors 57 to provide temperature sensing and control are then sewn in on the FIR fabric side at preferably a minimum 5 mm separation from any heating element 48 (and are electrically connected to one or more of the leg and system controller.

Figure 3:
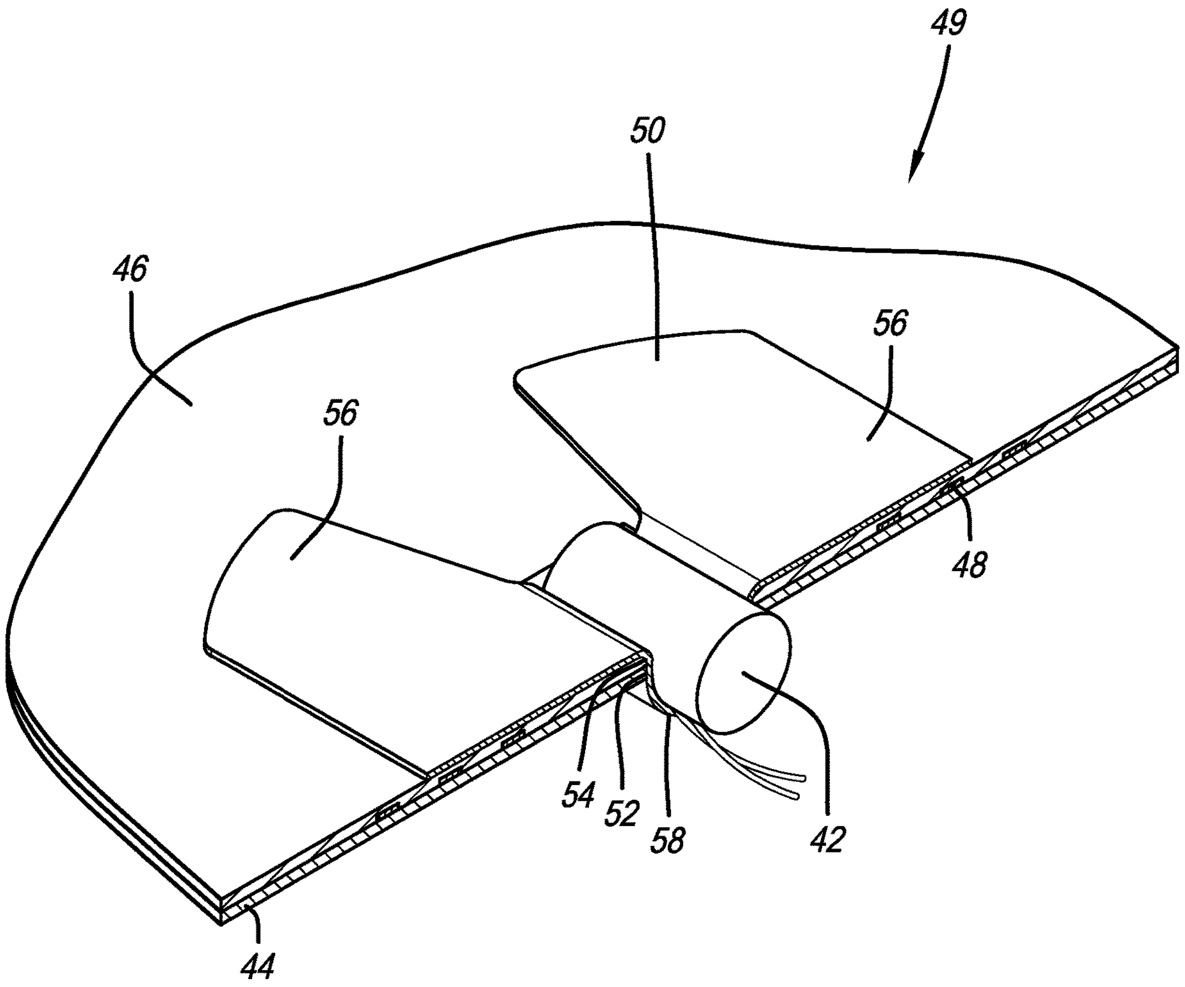
FIG. 3 is a cross-section of a portion of a vibration assembly.
Figure 4:
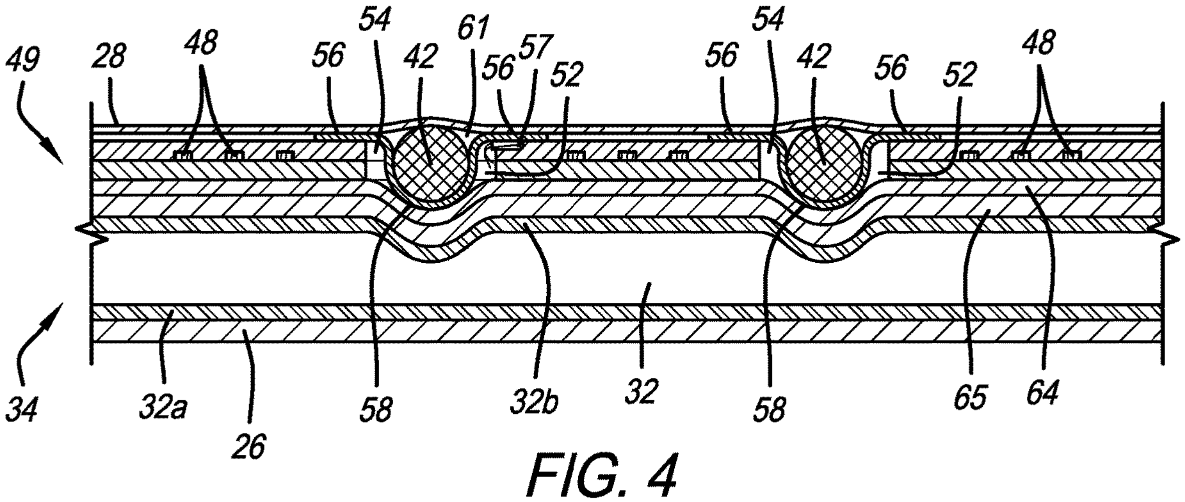
FIG. 4 is a cross-section through a wall of the sleeve.

In a preferred embodiment, each of the first, second and third vibration assemblies 36, 38 and 40 includes a plurality of motor securement members 50 for securing vibration motors 42 to one or both of the first and second carrier layers 44 and 46. In a preferred embodiment, the first carrier layer 44 includes a first carrier layer motor opening 52 defined therein and the second carrier layer 46 includes a second carrier layer motor opening 54 defined therein. When the first and second carrier layers are secured to one another (e.g., sewn to one another), the first and second carrier layer motor openings are aligned or registered with one another. As shown in FIG. 3, the motor securement member 50 includes first and second securing portions 56 and a motor portion 58 extending between the first and second securing portions 56. The first and second securing portions 56 are positioned on a first side of one of the carrier assembly 49 and secured thereto. In a preferred embodiment, at least a portion of the motor portion 58 of the motor securement member 50 and at least a portion of the vibration motor 42 extend through the first and second carrier layer motor openings 52 and 54, as is best shown in FIG. 1. The motor securement members 50 (as well as other layers, such as the inner and outer layers) can be made of nylon or other fabric. The vibration motors 42 can include double sided tape or other adhering member, glue, etc. thereon to connect or secure to the motor portion 58 of the motor secure member 50. Stitching can also be used.

As shown in FIG. 3, in a preferred embodiment, the motor portion 58 extends from one side of the carrier assembly to the opposite side of the carrier assembly, which defines a vibration motor pocket 61. In a preferred embodiment, the wires 59 or electrical contacts extend out of the vibration motor pocket 61 on the side of the carrier assembly 49 opposite the first and second securing portions 56.

Each of the second and third vibration assemblies 38 and 40 includes a plurality of vibration motors 42 that are each secured to the carrier assembly 49 and within the aligned first and second carrier layer motor openings by a plurality of motor securement members 50. In a preferred embodiment, the first vibration assembly 36 includes a multiple motor securement member 60 that comprises a central portion 62 and includes four motor portions 58 and four securing portions 56. With this arrangement, all four vibration motors can be secured within the first vibration assembly 36 using a single multiple motor securement member 60. Each of the carrier assemblies 49 can also include one or more thermistors 57.

In assembling the inner layer or leg facing layer with the carrier assembly, motor securement members, etc., the nylon motor securement members are placed in contact with the nylon inner or leg-facing layer, the thermistor and vibration motor electrical contacts or wires are accessible from the first carrier layer side, the thermistors are placed between the FIR fabric and the nylon inner layer, and heat press the panels to the nylon layer. In an exemplary embodiment, medium pressure is used for fifteen seconds at around 162° C.

Figure 2:
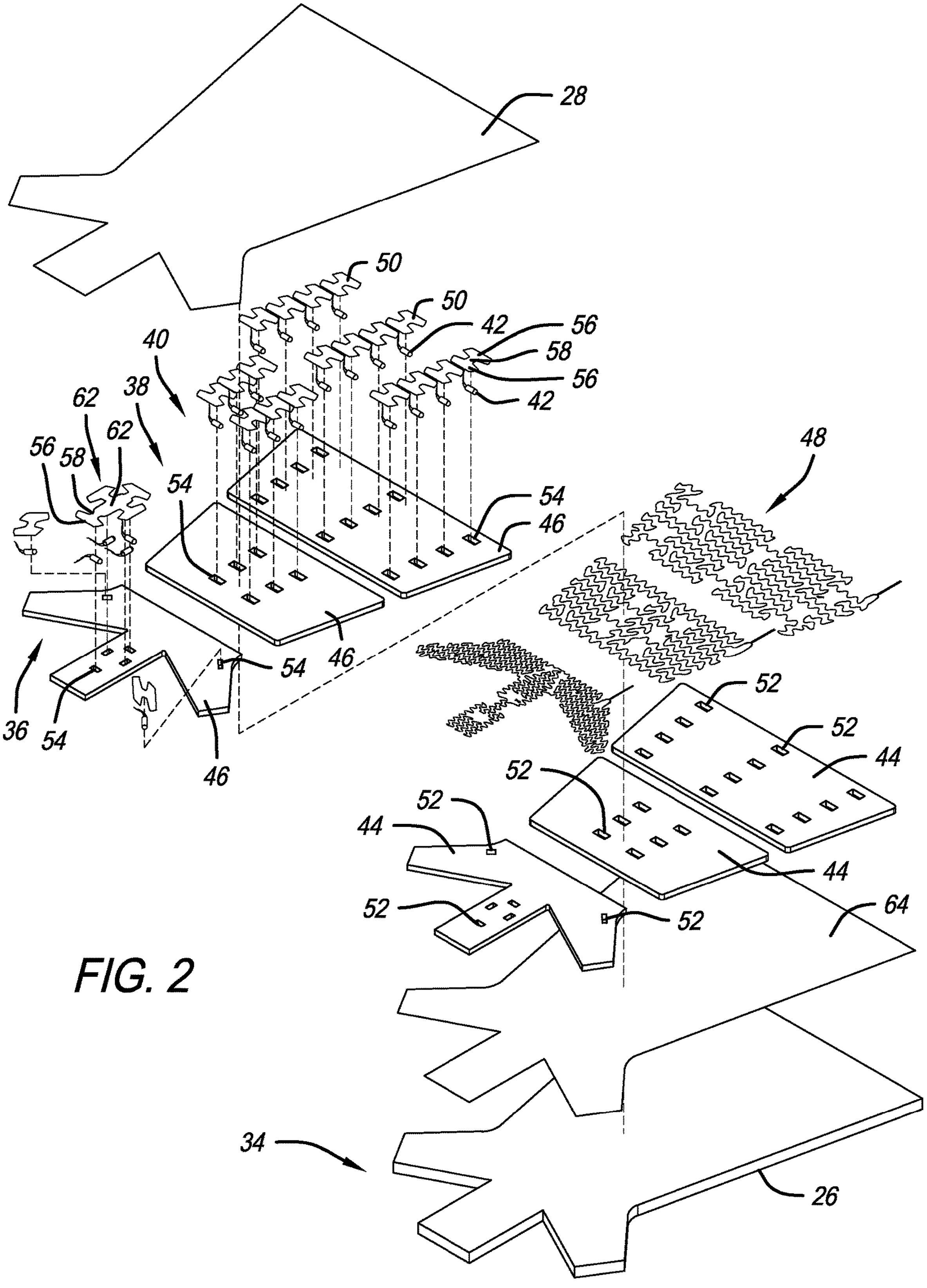
FIG. 2 is an exploded view of the pneumatic compression assembly.

It will be appreciated that the vibration motors 42 can be grouped into sets that can be vibrated or controlled separately. In a preferred embodiment, four sets of vibration motors are included, one set for the foot (the first vibration assembly 36), one set for the calf (the second vibration assembly 38) and two (e.g., upper and lower) sets for the thigh (the third vibration assembly 40). In a preferred embodiment, the pneumatic compression assembly 10 includes the same number sets of vibration motors as inflatable compartments 32 (e.g., four sets of vibration motors and four inflatable compartments—one for the foot, one for the calf and two for the upper leg). Any number of sets are within the scope of the present invention. As is shown in FIG. 2, the heating elements 48 are arranged with a plurality of bends, etc. to maximize coverage within the carrier assembly 49, vibration assembly or heating assembly. However, as is evident by the gaps between the heating elements in FIG. 2, gaps are provided so that there is no overlap of vibration motors with heating elements.

In a preferred embodiment, the pneumatic compression assembly 10 or sleeve 12 includes a reflective layer 64 (that may be a reflective foil) positioned between the carrier assembly 49 when one of the first and second carrier layers is a far infrared layer and the outer layer 26 of the sleeve. The reflective layer 64 reflects the infrared light or energy emitted from the infrared layer, fabric or lights and/or the user's body part and also helps maintain the heat between the reflective layer and the user's body part. The reflective layer acts as a passive infrared layer that holds or reflects infrared energy and heat (or cold) within the interior defined by the reflective layer.

It will be appreciated that the pneumatic compression assembly can include any or all of vibration, heating and/or infrared therapy. Accordingly, in another embodiment the vibration motors and associated motor securement members and motor openings can be omitted and the carrier assembly or a single carrier layer can include the heating element(s) thereon (referred to as a heat assembly). In another embodiment, the carrier assembly or a single carrier layer can be an infrared layer. In this embodiment only the infrared layer and possibly the reflective foil layer can be included.

Figure 5:
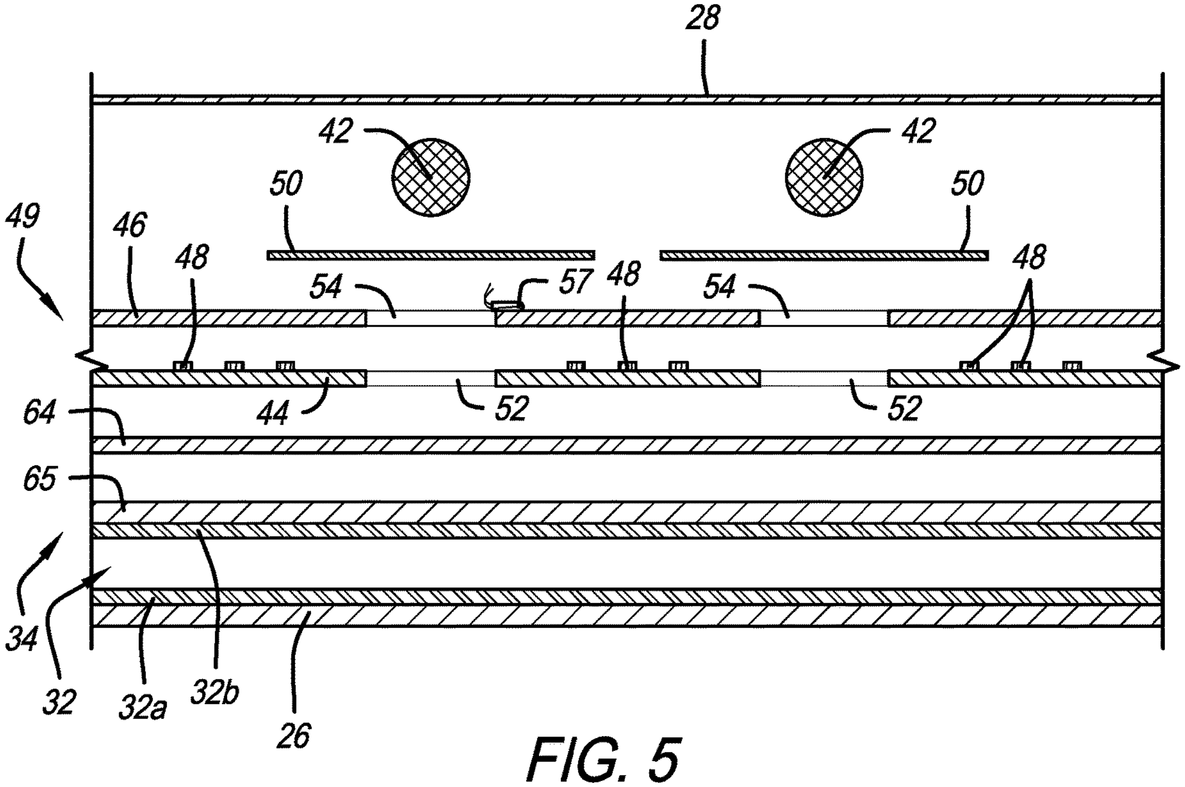
FIG. 5 is an exploded cross-section of the components in FIG. 4 before being assembled.

As shown in FIGS. 5, in a preferred embodiment, an inflatable compartment 32 includes first and second layers 32*a* and 32*b*. FIG. 5 also shows the outer layer 26 outside or adjacent to the inflatable compartment 32 and a layer 65 that separates the inflatable compartment from the vibration assembly or carrier assembly. The pneumatic compression portion 34 may include the outer layer 26 and layer 65 (preferably made of nylon or the like) with the inflatable compartments 32 sandwiched therebetween.

Figure 6:
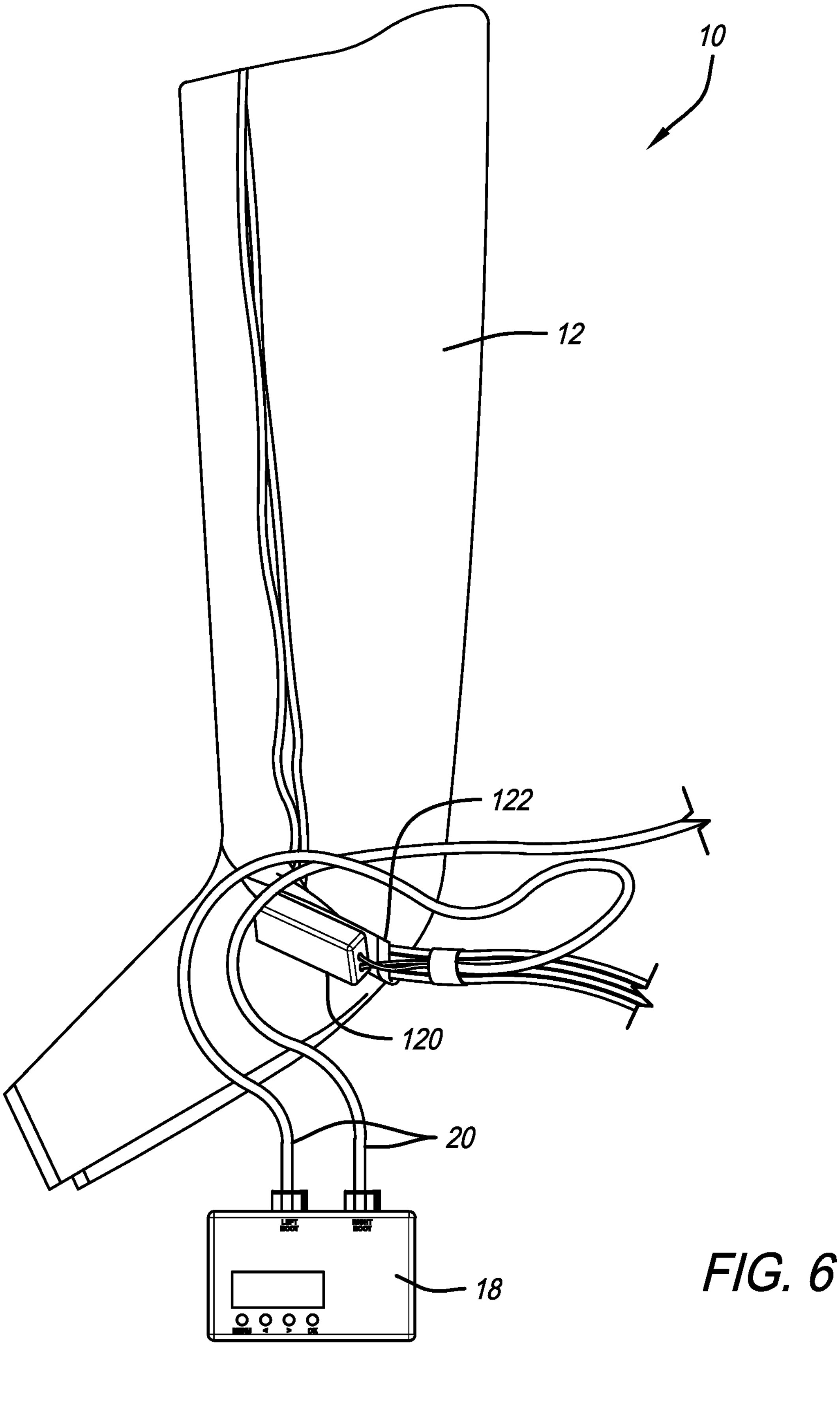
FIG. 6 is a perspective view of a pneumatic compression assembly showing the leg controller and system controller.
Figure 7:
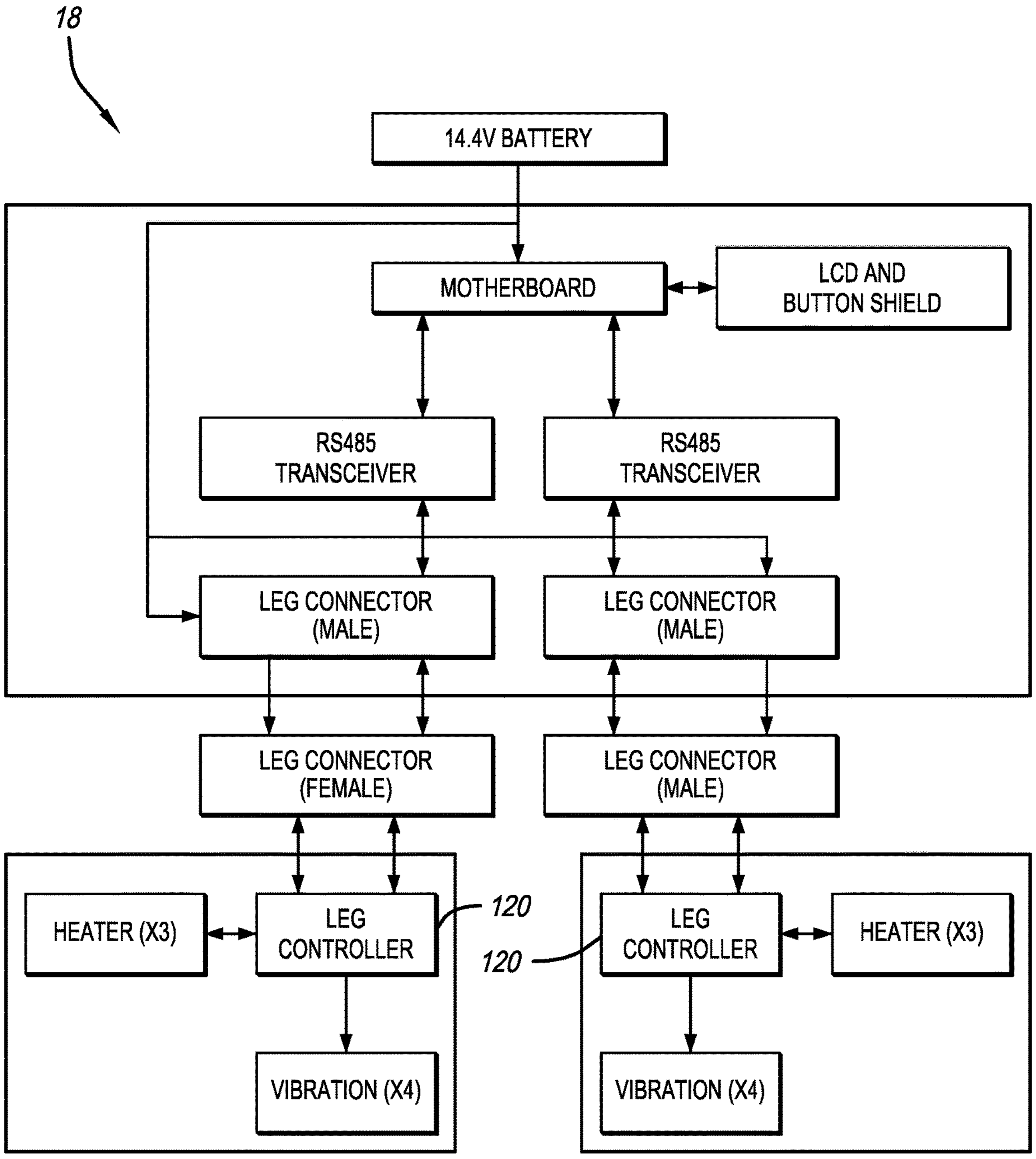
FIG. 7 is a flow chart depicting the control system.

As shown in FIG. 6, in a preferred embodiment, the pneumatic compression assembly 10 includes the main unit or system controller 18 that is configured to operate left and right boots or left and right pneumatic compression assemblies or systems. Furthermore, each (left and right) boot includes a separate controller or leg controller 120 in electrical and/or data communication with the system controller 18. In FIG. 6, the leg controller 120 is positioned underneath a flap 122. Preferably, the flap 122 (or other portion of the boot) also includes one or more tunnels or pockets extending therein through which the electrical cables and wires and/or pneumatic hoses, etc. can extend as they are routed to the various inflatable chambers, vibration motors or sets, heating elements and other components that are to be controlled, inflated/deflated or powered. In a preferred embodiment, a single console, system or device can include both the system controller and the pneumatic pump for controlling and inflating both boots. Separate connections for the electrical/data connection and pneumatic connection can be included. In a preferred embodiment, a single bundled connection member for each boot member that includes hoses to route air and cables for routing data and power is used (essentially combining cable 20 and hoses 22 into a single unit for each boot). In a preferred embodiment, data can be communicated wirelessly, such as via Bluetooth. FIG. 7 shows an exemplary chart that includes the system controller 18, left and right leg controllers 120 and various other components for controlling the heating, vibration, etc. in the boots/pneumatic compression assemblies. It will be appreciated that the system can include programming for different vibration and heat/cold intensities or levels, different lengths of time, only heating, only vibration, etc. as well as control of the pneumatic compression.

Figure 8:
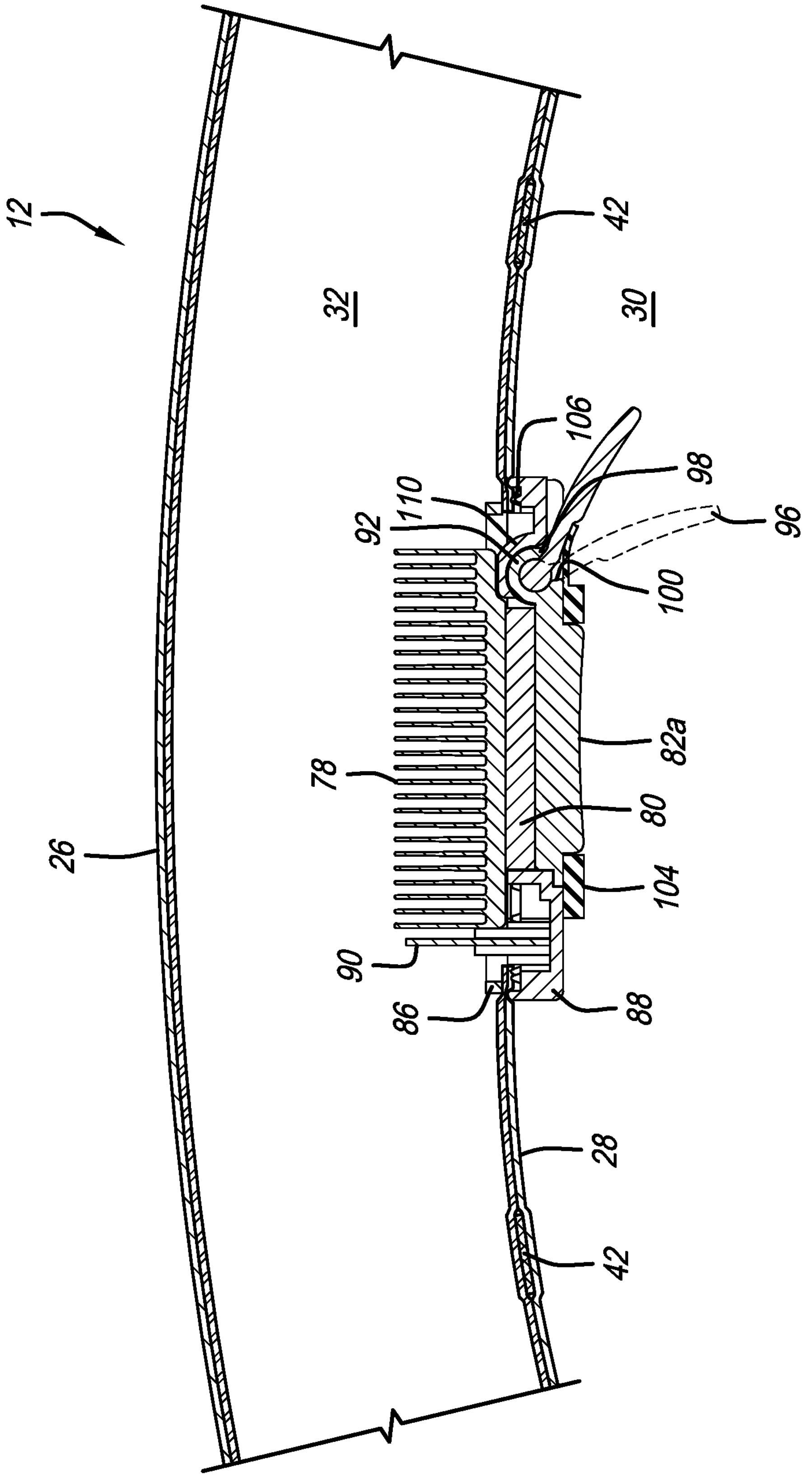
FIG. 8 is cross-section through the sleeve viewed from the top and showing a temperature control module therein.

FIGS. 8-11 show another embodiment of a pneumatic compression assembly 70 that includes one or more temperature control modules 72 positioned within or on the sleeve 12. As shown in FIG. 8, in a preferred embodiment, one or more temperature control modules 72 are included or positioned in one or more of the inflatable compartments 32. In a preferred embodiment, the temperature control module 72 includes a housing 74, a fan 76, a heat sink 78, a thermoelectric cooler, peltier device or controllable temperature element 80, a spreader plate or member 82 and a plurality of finger spreaders 84 that are pivotably attached to the spreader member 82. In a preferred embodiment, the housing 74 includes an upper portion 86 and a lower portion 88. In use, the lower surface 82*a* of the spreader member 82 and the inner or lower surface 84*a* of the finger spreader(s) 84 are positioned to contact and transfer thermal energy (hot or cold) to the user's body part. As discussed above and herein, the lower surface of the controllable temperature element 80 is configured to transfer thermal energy to the upper surface of the spreader member 82 and heat sink 78 is configured to pull heat from the upper surface of the controllable temperature element 80. The fan 78 helps dissipate heat from the heat sink 78 and other components. In use, the primary spreader member 82 is cooled or heated by the controllable temperature element 80 and the heat or cold is conducted from the primary spreader 82 to the finger spreaders 84. In a preferred embodiment, the temperature control module 72 also includes a PCB 90 for electrical and data communication (with the system controller 18 or other controller) and controlling the module.

Figure 9:
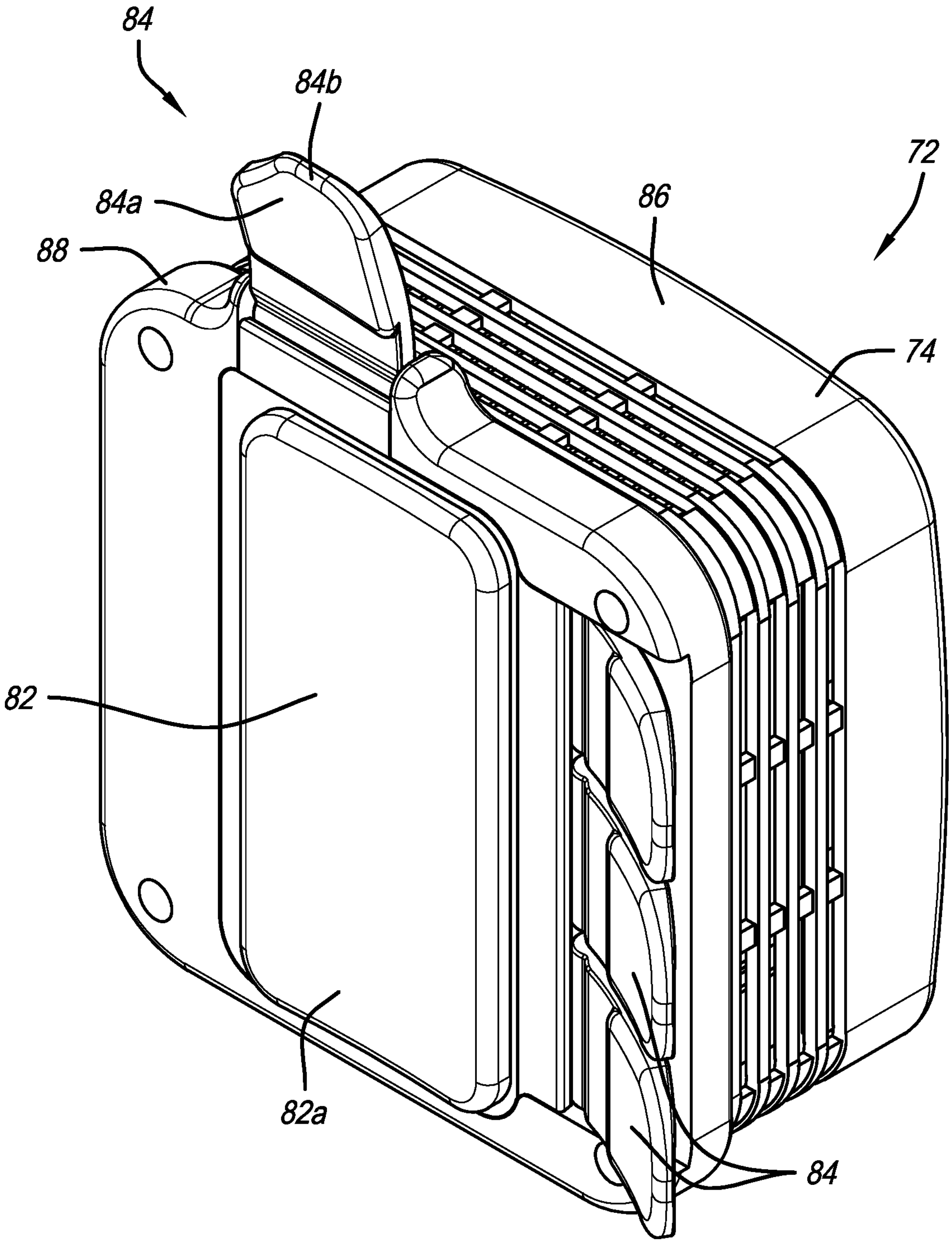
FIG. 9 is a perspective view of a temperature control module.
Figure 10:
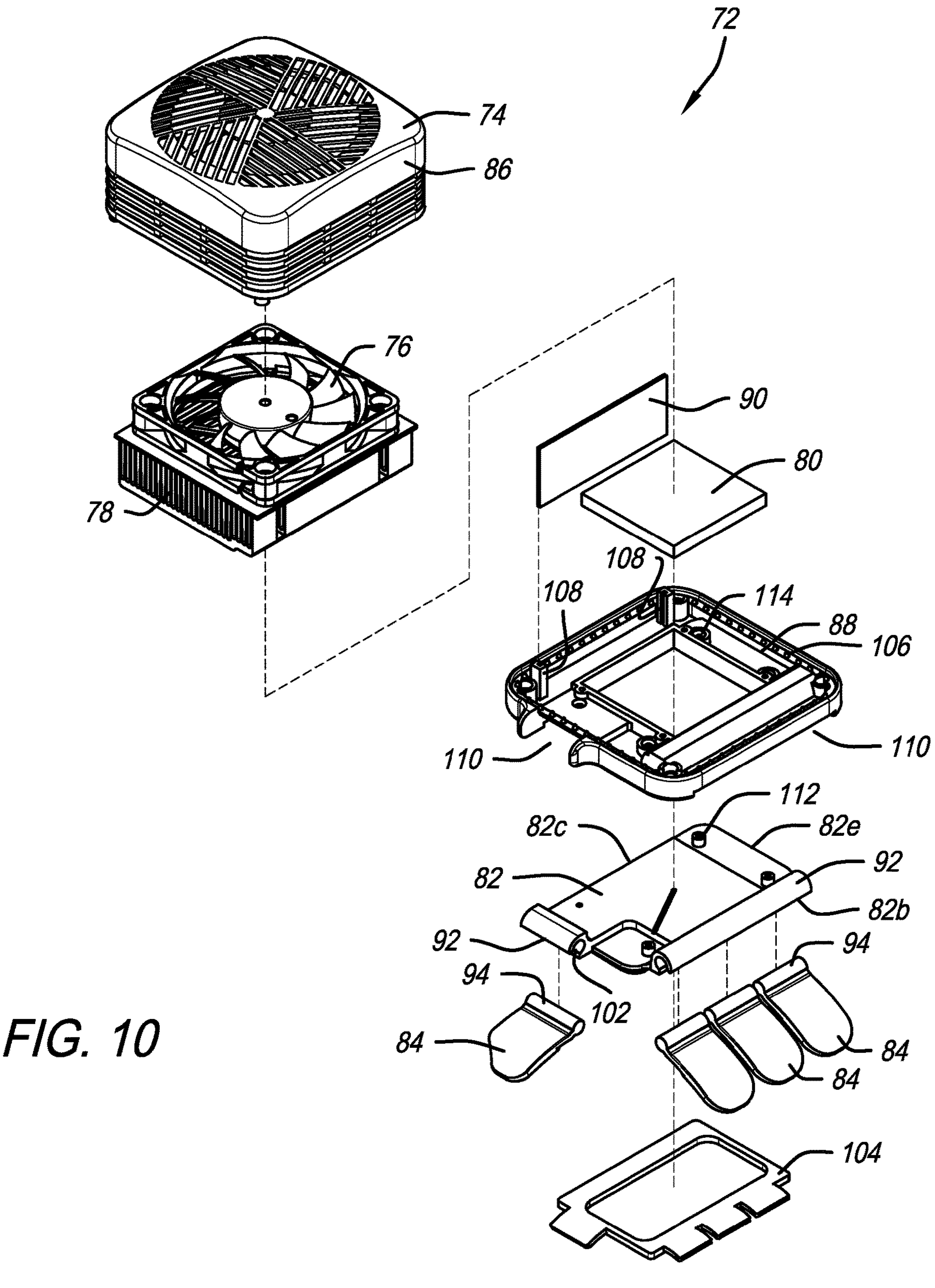
FIG. 10 is an exploded perspective view of the temperature control module.

In a preferred embodiment, the spreader member 82 is configured to conduct thermal energy to the finger spreaders 84. The spreader member 82 includes first and second opposing edges 82*b* and 82*c* and third and fourth opposing edges 82*d* and 82*e*. In a preferred embodiment, finger spreaders 84 extend from and/or past a plurality of the outer edges of the spreader member. For example, as shown in FIGS. 9-10, three finger spreaders 84 extend from the first edge 82*b* and one finger spreader extends from the third edge 82*d*. In another embodiment, one or more finger spreaders can extend from all or three edges.

Any type of pivotable connection between the finger spreaders and the spreader member is within the scope of the present invention. In a preferred embodiment, the finger spreaders 84 are hingedly attached to the spreader member 82. To provide the hinged connection, the spreader member 82 includes one or more knuckle portions 92 and the finger spreaders 84 include a pin portion 94 that is received in the knuckle portion 92. The contact portion 96 of the finger spreader 84 extends outside of knuckle portion 92 and the pin portion 94 is rotatable within the knuckle portion 92. FIG. 8 shows the finger spreader 84 in a first position in solid lines and a second position in dashed lines. In a preferred embodiment, in at least the second position, a distal end 84*b* of the finger spreader(s) 84 is positioned below the lower surface 82*a* of the spreader member 82.

In a preferred embodiment, the knuckle portion 92 includes upper and lower stop members 98 and 100 that include a pivot space 102 therebetween. The finger spreaders 84 are pivotable within the pivot space 102 and between the upper and lower stop members 98 and 100. The upper and lower stop members 98 and 100 define the upper and lower limits of the pivot angle of the finger spreaders. FIG. 8 shows the finger spreader 84 in the first position in solid lines and with the upper surface against the upper stop member 98 and in the second position in dashed lines with the lower surface against the lower stop member 100.

As shown in FIGS. 8 and 10, in a preferred embodiment, the temperature control module 72 includes a pad member 104 that at least partially covers the spreader member 82 and allows the contact portion 106 of the spreader member to extend there around or below (see FIG. 8). The pad member 104 can be included to improve comfort. For example, it can be made of a soft material, such as TPE rubber or other rubber and overmolded onto the plastic lower portion of the housing.

It will be appreciated that in pneumatic compression assemblies for different portions of the body, different numbers of finger spreaders can be used in different places or extending from different sides of the main spreader member 82 in order to accommodate different portions, parts or shapes of the human anatomy. For example, as shown in FIG. 9, the temperature control module 72 include three finger spreaders 84 extending outwardly therefrom in one direction and one finger spreader 84 extending in a second direction. The separate finger spreaders 84 provide flexibility to adapt to different sized user's body parts and geometries. When the sleeve portion 12 is wrapped around the user's leg and the inflatable compartments are inflated, the inner layer 28 or other layer contacts the upper surface of the finger spreader 84 and pivots the finger spreader 84 into contact with the user's skin.

As shown in FIG. 8, in a preferred embodiment, one or more layers (e.g., the inner layer or a layer associated with the inflatable compartment are sandwiched between the upper portion 86 and the lower portion 88 of the housing 74. Preferably, the lower portion 88 includes a plurality of spike members 106 that engage the layer(s) sandwiched therebetween and help hold the temperature control module 72 in place. As shown in FIG. 10, the lower portion 88 also includes rails 108 that contain the ends of the PCB 90. The lower portion 88 also includes knuckle portion recesses 110 in which the knuckle portions 92 of the spreader member 82 is received. Preferably, registration members 112 extend upwardly from the upper surface of the spreader member 82 and are received in registration openings 114 defined in the lower portion 88 of the housing 74. It will be appreciated that in FIGS. 9 and 10, the upper portion 86 of the housing covers the fan and heat sink. In another embodiment, as shown in FIG. 8, the housing can be truncated and the fan can be omitted. In this embodiment, the air moving through the inflatable compartment(s) 32 as a result of the pump passes over the heat sink 78 and cools the temperature control module 72. In another embodiment the heat sink can also be omitted with the air in the sleeve cooling the temperature control element 80. In a preferred embodiment, vibration motors 42 can also be included in the sleeve 12 and positioned adjacent the user's skin, as shown in FIG. 8

Figure 11:
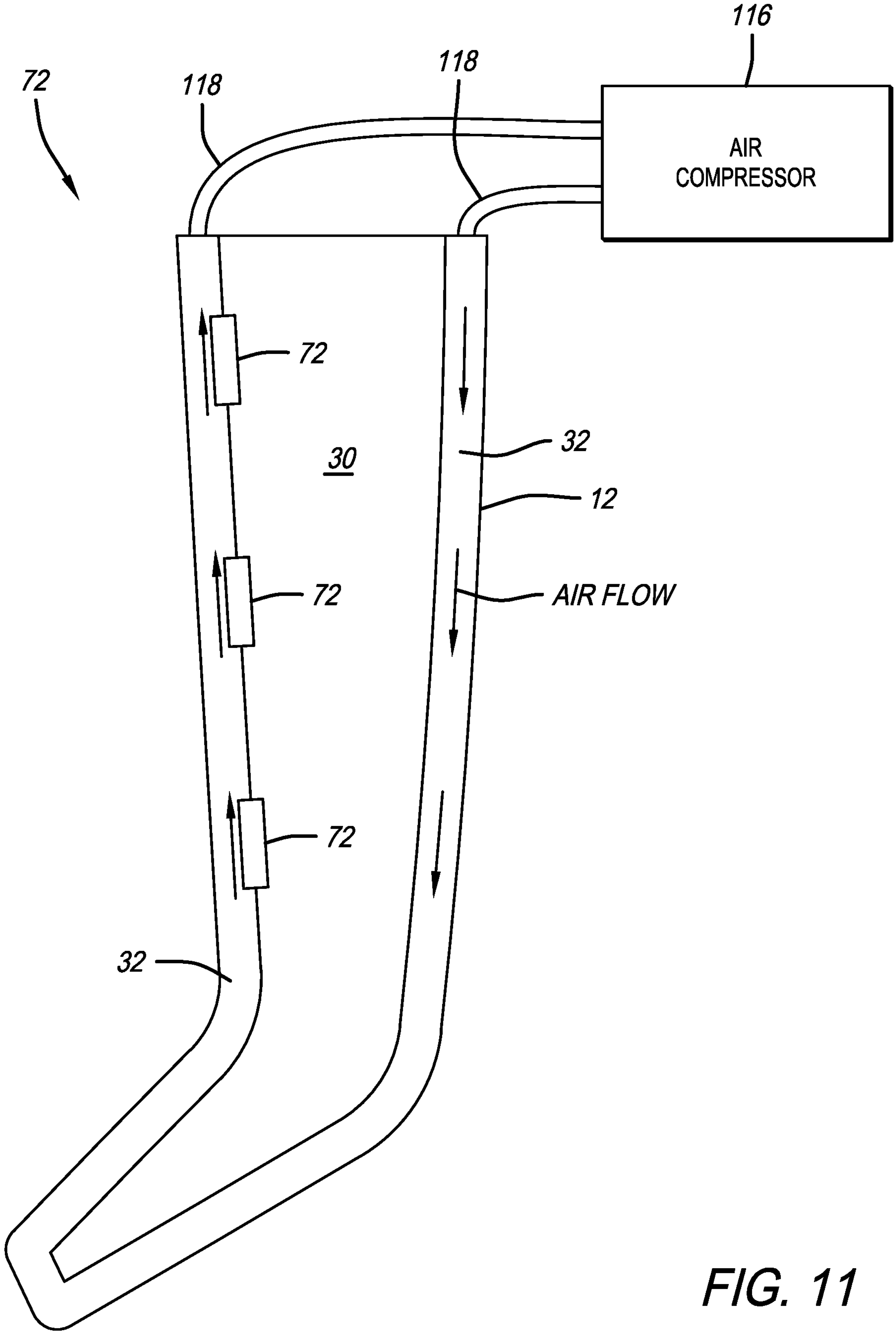
FIG. 11 is a schematic view of a pneumatic compression assembly with temperature control modules therein and showing air flow therethrough.

FIG. 11 shows an embodiment of the pneumatic compression assembly 70 with a plurality of temperature control modules 72 therein and with arrows showing the direction of the air pumping through the one or more inflatable compartments and cooling the temperature control modules. See the air compressor or pump 116 and the hoses 118 connected thereto for moving air into and out of the sleeve 12.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A pneumatic compression assembly, comprising:

a sleeve that includes an outer layer and an inner layer that define a sleeve interior configured to receive a body part of a user, the sleeve comprising a foot portion and a leg portion;

a plurality of inflatable compartments arranged longitudinally along the sleeve between the inner layer and the outer layer, wherein each of the plurality of inflatable compartments is configured to inflate to provide compression to the body part of the user independently without inflating the sleeve as a whole;

a vibration assembly configured to provide vibration to the body part of the user, wherein the vibration assembly includes:

a plurality of vibration motors positioned between the inner layer and the outer layer of the sleeve;

a first carrier layer made of fabric; and a first motor securement member, wherein the first motor securement member is secured to the first carrier layer on a first side and secured to the first of the plurality of vibration motors on a second side opposite the first side;

a flap located on the sleeve and closer to the foot portion than to the leg portion, the flap defining a single inlet;

hoses extending through the single inlet to route air from a pump to each of the plurality of inflatable compartments; and a system controller extending through the single inlet through a single cable and configured to control each of the plurality of inflatable compartments independently and sequentially to provide compression and the vibration assembly to provide vibration.

2. The pneumatic compression assembly of claim 1, wherein the first carrier layer includes a first carrier layer motor opening defined therein, wherein the first motor securement member includes first and second securing portions and a motor portion extending between the first and the second securing portions, wherein the first and the second securing portions are positioned on a first side of the first carrier layer, and wherein a portion of the motor portion of the first motor securement member and a portion of the first of the plurality of vibration motors partially extend through the first carrier layer motor opening.

3. The pneumatic compression assembly of claim 2, wherein the first carrier layer further includes a heating element thereon.

4. The pneumatic compression assembly of claim 3, wherein the vibration assembly further comprises a second carrier layer positioned between the inner layer and the outer layer of the sleeve.

5. The pneumatic compression assembly of claim 4, wherein the second carrier layer is secured to the first carrier layer and sandwiches the heating element therebetween.

6. The pneumatic compression assembly of claim 5, wherein the second carrier layer includes a second carrier layer motor opening defined therein, wherein the first and the second securing portions are positioned on a first side of the second carrier layer, and wherein at least a portion of the motor portion of the first motor securement member and at least a portion of the first of the plurality of vibration motors extend through the first and the second carrier layer motor openings.

7. The pneumatic compression assembly of claim 6, wherein at least one of the first and the second carrier layers comprises an infrared layer.

8. The pneumatic compression assembly of claim 7, wherein the infrared layer comprises one or more infrared light-emitting diodes.

9. The pneumatic compression assembly of claim 1, further comprising a heating assembly configured to provide heat to the body part of the user, wherein the heating assembly is positioned between the inner layer and the outer layer of the sleeve.

10. The pneumatic compression assembly of claim 1, further comprising a plurality of thermistors arranged between the inner layer and the outer layer of the sleeve.

11. The pneumatic compression assembly of claim 1, wherein the hoses are bundled into a single unit.

12. The pneumatic compression assembly of claim 1, further comprising a leg controller coupled to the flap and in electric connection with the system controller.

13. The pneumatic compression assembly of claim 1, wherein the sleeve further comprises a calf portion, and wherein the plurality of vibration motors is arranged in different groups of vibration motors for the foot portion, the calf portion, and the leg portion.

14. The pneumatic compression assembly of claim 13, wherein the system controller is further configured to control vibration of the different groups of vibration motors independently.

15. The pneumatic compression assembly of claim 14, wherein the different groups of vibration motors comprise a first group for the foot portion, a second group for the calf portion, a third group for the leg portion, and a fourth group for the leg portion.

16. A pneumatic compression assembly, comprising:

a sleeve that includes an outer layer and an inner layer that defines a sleeve interior configured to receive a body part of a user, the sleeve comprising a foot portion and a leg portion;

a plurality of inflatable compartments arranged longitudinally along the sleeve between the inner layer and the outer layer, wherein each of the plurality of inflatable compartments is configured to inflate to provide compression to the body part of the user independently without inflating the sleeve as a whole;

a vibration assembly configured to provide vibration to the body part of the user positioned between at least one of the plurality of inflatable compartments and the inner layer, wherein the vibration assembly includes a first carrier layer that includes a first carrier layer motor opening defined therein, a second carrier layer that includes a second carrier layer motor opening defined therein, a vibration motor, and a motor securement member, wherein the first and the second carrier layers are secured to one another to form a carrier assembly, wherein the motor securement member includes first and second securing portions and a motor portion extending between the first and the second securing portions, wherein the first and the second securing portions are positioned on a first side of the carrier assembly, wherein the motor securement member is secured to the first carrier layer on a first side and secured to the vibration motor on a second side opposite the first side, wherein a portion of the motor portion and a portion of the vibration motor partially extend through the first and the second carrier layer motor openings, and wherein the first carrier layer includes a heating element thereon and is made of fabric;

a flap located on the sleeve and closer to the foot portion than to the leg portion, the flap defining a single inlet;

hoses extending through the single inlet to route air from a pump to each of the plurality of inflatable compartments; and a system controller extending through the single inlet through a single cable and configured to control each of the plurality of inflatable compartments independently and sequentially to provide compression and the vibration assembly to provide vibration.

17. The pneumatic compression assembly of claim 16, wherein at least one of the first and the second carrier layers comprises an infrared layer.

18. A pneumatic compression assembly, comprising:

a sleeve that includes an outer layer and an inner layer that defines a sleeve interior configured to receive a body part of a user, the sleeve comprising a foot portion and a leg portion;

a plurality of inflatable compartments arranged longitudinally along the sleeve between the inner layer and the outer layer, wherein each of the plurality of inflatable compartments is configured to inflate to provide compression to the body part of the user independently without inflating the sleeve as a whole;

a temperature control module coupled within the sleeve, wherein the temperature control module includes a housing, a controllable temperature element, and a spreader member, wherein a lower surface of the spreader member is positioned to directly contact the body part of the user, and wherein the controllable temperature element is configured to transfer thermal energy to an upper surface of the spreader member;

a flap located on the sleeve and closer to the foot portion than to the leg portion, the flap defining a single inlet;

hoses extending through the single inlet to route air from a pump to each of the plurality of inflatable compartments; and a system controller extending through the single inlet through a single cable and configured to control each of the plurality of inflatable compartments independently and sequentially to provide compression.

19. The pneumatic compression assembly of claim 18, wherein the temperature control module includes a heat sink that is positioned within a first of the plurality of inflatable compartments, whereby air moving through the first of the plurality of inflatable compartments pulls heat from the heat sink.

* * * * *